United States Patent [19]

Harre et al.

[11] Patent Number: 5,288,878
[45] Date of Patent: Feb. 22, 1994

[54] (1S,2S,3R,5R)-2-[(3S)-2-HALO-3-HYDROXY-1-ALKEN(YNYL)]-3-TRIALKYLSILYLOXY-7,7-(2,2-DIMETHYL-TRIMETHYLENEDIOXY)-BICYCLO[3.3.0]OCTANE COMPOUNDS AND PROCESSES FOR THEIR PREPARATION

[75] Inventors: Michael Harre; Jürgen Westermann, both of Berlin, Fed. Rep. of Germany

[73] Assignee: Schering Aktiengesellschaft, Berlin and Bergkamen, Fed. Rep. of Germany

[21] Appl. No.: 689,247

[22] PCT Filed: Oct. 13, 1989

[86] PCT No.: PCT/DE89/00660

§ 371 Date: Jun. 12, 1991

§ 102(e) Date: Jun. 12, 1991

[87] PCT Pub. No.: WO90/03974

PCT Pub. Date: Apr. 19, 1990

[51] Int. Cl.[5] ............................................. C07D 319/06
[52] U.S. Cl. .................................... 549/214; 562/501
[58] Field of Search .............. 549/336, 214; 562/501

[56] References Cited

U.S. PATENT DOCUMENTS

| | | | |
|---|---|---|---|
| 4,322,435 | 3/1982 | Kojima et al. | 549/336 |
| 4,423,067 | 12/1983 | Skuballa et al. | 562/501 |
| 4,925,956 | 5/1990 | Skuballa et al. | 562/501 |
| 5,013,758 | 5/1991 | Skuballa et al. | 562/501 |

FOREIGN PATENT DOCUMENTS

| | | |
|---|---|---|
| 0234158 | 9/1987 | European Pat. Off. |
| 0268548 | 5/1988 | European Pat. Off. |
| 3203687 | 8/1988 | Japan |

OTHER PUBLICATIONS

Corey et al. "Total Synthesis of $C_{22}$-Prostanoids in the E and F Series Based on Docosahexaenoic Acid" J. Am. Chem. Soc. 1984, 106, 3875-3876.

*Primary Examiner*—C. Warren Ivy
*Assistant Examiner*—A. A. Owens

*Attorney, Agent, or Firm*—Millen, White, Zelano, & Branigan

[57] ABSTRACT

The invention concerns a process for preparing (1S,2S,3R,5R)-2-[(3S)-2-halo-3-hydroxy-1-alken(ynyl)]-3-trialkylsilyloxy-7,7-(2,2-dimethyltrimethylenedioxy)-bicyclo[3.3.0]octane compounds of general Formula I

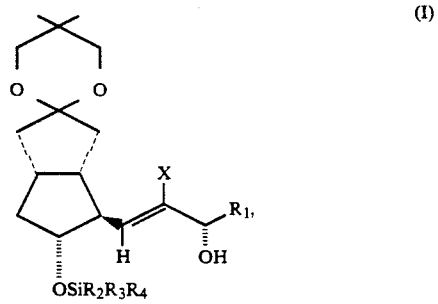

wherein
X is chlorine or bromine,
$R_1$ can mean straight-chain or branched alkyl of up to 6 carbon atoms, straight-chain or branched alkenyl of up to 6 carbon atoms, straight-chain or branched alkynyl of up to 6 carbon atoms,
$R_2$, $R_3$, $R_4$ can be in each case identical or different and can mean $C_1$–$C_4$-alkyl and phenyl optionally substituted by $C_1$–$C_4$-alkyl groups, wherein the 13,14-double bond has the trans configuration with respect to the C chain, by stereoselective reduction of an α-halo-enone of general Formula II (Abstract continued on next page.)

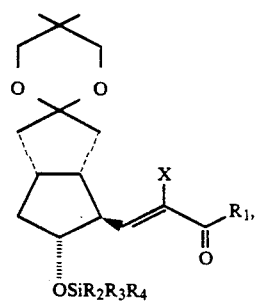
(II) wherein X, $R_1$, $R_2$, $R_3$, $R_4$ have the meanings given above,
with a reagent produced from diisobutyl aluminum hydride and 2,6-di-tert-butyl-4-methylphenol.
12 Claims, No Drawings

(1S,2S,3R,5R)-2-[(3S)-2-HALO-3-HYDROXY-1-ALKEN(YNYL)]-3-TRIALKYLSILYLOXY-7,7-(2,2-DIMETHYL-TRIMETHYLENEDIOXY)BICYCLO[3.3.0]OCTANE COMPOUNDS AND PROCESSES FOR THEIR PREPARATION

The invention relates to a novel process for the preparation of (1S,2S,3R,5R)-2-[(3S)-2-halo-3-hydroxy-1-alken(ynyl)]-3-trialkylsilyloxy-7,7-(2,2-dimethyltrimethylenedioxy)bicyclo[3.3.0]octane compounds by reduction of 15-ketocarbacyclin intermediates (PG nomenclature) with diisobutyl aluminum 2,6-di-tert-butyl-4-methylphenoxide.

The reduction of the 15-keto group to the 15α-hydroxy group at an intermediate stage of the synthesis plays an important part in the syntheses of the pharmacologically active carbacyclin analogs "Cicaprost"

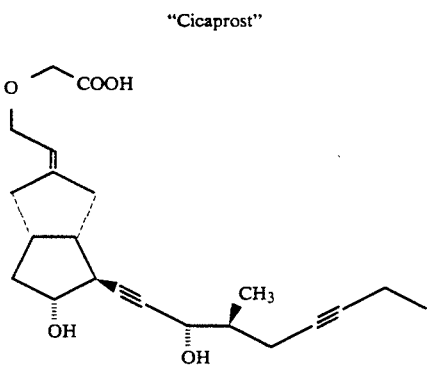

and, respectively, "Eptaloprost"

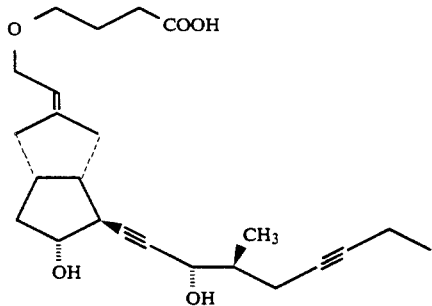

Reduction with technically readily accessible reagents, such as sodium borohydride, leads to a mixture with the undesirable 15α-hydroxy epimer. The two epimers must be separated from each other by chromatography. (For economical reasons, the 15α-hydroxy epimer must be reoxidized and again reduced and separated into the 15-epimers, and so forth.)

The amount of adsorbent and solvent quantity required for separation is the higher, the more 15α-hydroxy epimer must be segregated. In accordance with the methods known heretofore, working with simple hydride reagents, a relatively high expenditure is necessary for preparing the 15α-hydroxy epimers. Therefore, the problem to be solved resides in further improving the chemical reduction of the 15-keto group in the sythesis of carbacyclin analogs with respect to the yield of 15α-hydroxy epimer.

The invention relates to a process for preparing (1S,2S,3R,5R)-2-[(3S)-2-halo-3-hydroxy-1-alken(ynyl)]-3-trialkylsilyloxy-7,7-(2,2-dimethyltrimethylenedioxy)-bicyclo[3.3.0]octane compounds of general Formula I

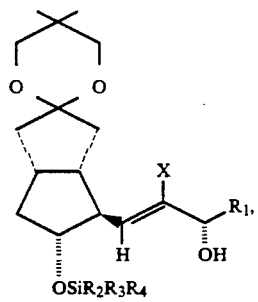

wherein

X is chlorine or bromine, $R_1$ can mean straight-chain or branched alkyl of up to 6 carbon atoms, straight-chain or branched alkenyl of up to 6 carbon atoms, straight-chain or branched alkynyl of up to 6 carbon atoms, $R_2$, $R_3$, $R_4$ can be in each case identical or different and can mean $C_1$–$C_4$-alkyl and phenyl optionally substituted by $C_1$–$C_4$-alkyl groups, wherein the 13,14-double bond has the trans configuration with respect to the C chain, by stereoselective reduction of an α-halo-enone of general Formula II

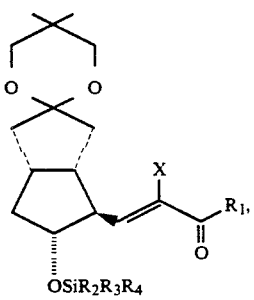

wherein X, $R_1$, $R_2$, $R_3$, $R_4$ have the meanings given above, with a reagent produced from diisobutyl aluminum hydride and 2,6-di-tert-butyl-4-methylphenol.

The thus-prepared optical isomers exhibit the same relative stereochemical configuration as the corresponding prostacyclin from mammalian tissue, or, in case of an intermediate product, the stereochemical configuration that would be displayed by a prostacyclin-like product having the same relative stereochemical configuration as prostacyclin from mammalian tissue.

A primary problem in the synthesis of carbacyclins, prostaglandins and prostacyclins is presented by the stereoselective introduction of functional groups. The stereochemical control at C15 in the conformationally movable side chain causes special problems.

It is therefore very often desirable to produce the 15α-hydroxy epimer with preference over the 15β-hydroxy epimer since this stereochemical arrangement remains preserved during the subsequent conversions into prostacyclin-type compounds in accordance with conventional methods. Consequently, compounds are obtained with the identical configuration at C15 as PGF2α with the desirable pharmacological properties.

Heretofore, the 15-hydroxy group has been prepared by reduction of the 15-ketone, using as the reducing agents NaBH₄, NaBH₄/CeCl₃, Zn(BH₄)₂.

The aforementioned reducing agents, however, exhibit the drawback that they yield mixtures of 15-hydroxy epimers. Other reducing agents, such as "S-Binal-H", do provide a high stereoselectivity in favor of the 15α-hydroxy epimer, but are more expensive, can be utilized only at low temperatures (−100° to −110° C.), and in addition must be employed in a high excess.

Occasionally, stereoselectivity of the reduction is linked to the type of blocking group at C11. For example, a 15α/15β proportion of 92:8 was achieved with a p-phenylphenylcarbamoyl group and a sterically hindered lithium or potassium trialkyl hydridoborate at −130° C.

Another reducing agent is diisobutyl aluminum 2,6-di-tert-butyl-4-methylphenoxide. This compound can be used in order to perform the 15-keto reduction in various prostaglandins and prostacyclins.

Although EP 234,158 cites, as a possible reducing agent for isocarbacyclin intermediates, diisobutyl aluminum 2,6-di-tert-butyl-4-methylphenoxide, this application contains not a single practical example. E. J. Corey et al., JACS 106:3875 (1984) and W. Bartmann et al., Ann. 321 (1987) obtained high yields of 15α-hydroxy epimers from not halogenated enones only with a high excess of reagent with up to 10 equivalents which, however, makes working up difficult. In order to achieve the high stereoselectivities, though, a hydroxy group must be present in the 11-position.

A free 11-hydroxy group, however, represents a disadvantage in synthesis because it can interfere in additional reactions to build up the prostacyclin.

As demonstrated by Table 1, the 15-keto reduction on compounds having a blocked 11-hydroxy group results in substantially lower stereoselectivities

TABLE 1

| Ketone | Equivalents DIBAL-H/"Ionol" | 15α/15β |
|---|---|---|
| R = H | 10 | 91:9 |
| R = Ac | 10 | 50:50 |
| R = THP | 10 | 66:34 |
| R = φ-φ-C(=O)- | 10 | 50:50 |

TABLE 1-continued

| | | |
|---|---|---|
| R = H | 6 | 99:1 |
| R = φ-φ-C(=O)- | 6 | 61:39 |

φ-φ-C(=O)- = p-Phenylbenzoyl

It has now been found that the α-halo-enones (1), (2), (3), (4), (5), (6), blocked in the 11-position with silyl ethers (TBDMS=tert-butyldimethylsilyloxy or TBDPS=tert-butyldiphenylsilyloxy) are reduced to the 15α-hydroxy epimers with 1.1 to 1.5 equivalents of diisobutyl aluminum 2,6-di-tert-butyl-4-methylphenoxide in toluene at −70° C. to −80° C. in four hours in high yields of about 80% of theory and high stereoselectivity (ratio of epimers 92.7-97.4%), wherein the only minor excess of reagent makes a simple working up operation possible.

The following tabular overview serves as a confirmation for the process of this invention:

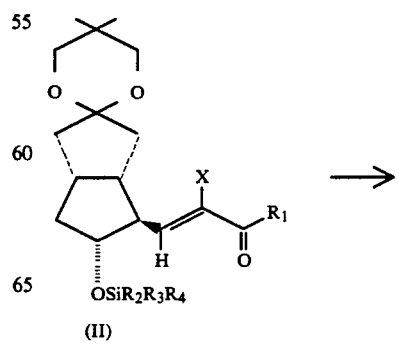

(II)

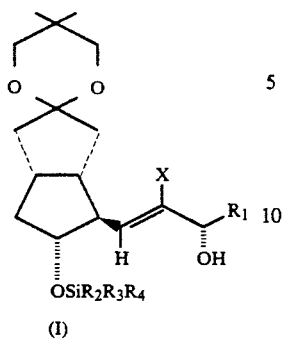

(I)

TABLE 2

| Ketone No. | X | R2 | R3 | R4 | R1 | Alcohol No. | 15α/15β |
|---|---|---|---|---|---|---|---|
| (1) | Br | t-Bu | Me | Me | CH₃⋯H (propargyl) | (7) | 97.4:2.6 |
| (2) | Br | t-Bu | Me | Me | H⋯CH₃ (propargyl) | (8) | 92.7:7.3 |
| (3) | Cl | t-Bu | Me | Me | CH₃⋯H (propargyl) | (9) | 97.0:3.0 |
| (4) | Cl | t-Bu | Me | Me | H⋯CH₃ (propargyl) | (10) | 96.4:3.6 |
| (5) | Br | t-Bu | Me | Me | H H (pentyl) | (11) | 88.0:12.0 |
| (6) | Br | t-Bu | φ | φ | CH₃⋯H (propargyl) | (12) | 92.6:7.4 |
| (13) | H | t-Bu | Me | Me | CH₃ | | 50:50 |
| (14) | H | t-Bu | Me | Me | C₅H₁₁ | | 50:50 |
| (15) | H | t-Bu | Me | Me | CH₃⋯H (propargyl) | | 50:50 |
| (16) | H | t-Bu | Me | Me | H⋯CH₃ (propargyl) | | 50:50 |

φ = Phenyl

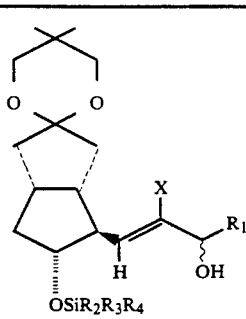

In contrast thereto, the not halogenated ketones (13), (14), (15) and (16), blocked in the 11-position, are reduced at −78° C. even with 20 equivalents of the same reducing agent merely to an extent of about 10%, and without any stereoselectivity.

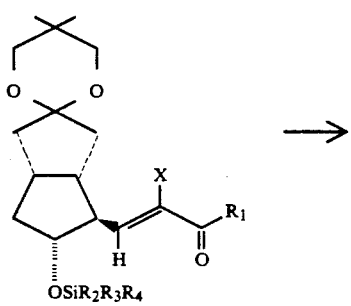

The stereoselective reduction according to this invention is performed at low temperatures of −40° C. to −100° C., preferably at −70° C. to −80° C. The diluent for the reaction is toluene; other solvents, such as tetrahydrofuran, ether, hexane, dimethoxyethane, reduce stereoselectivity.

The reduction is preferably carried out with a slight excess of diisobutyl aluminum 2,6-di-tert-butyl-4-methylphenoxide (1.1–1.5 equivalents) 10 in order to ensure a complete reaction.

The reaction time ranges between 1 and 12 hours, preferably 2–4 hours. The working up operation is suitably effected by alcoholysis of the aluminate with isopropanol and subsequent decomposition with water, suctioning off the precipitated aluminum hydroxide, drying, and concentration of the organic phase under vacuum.

The production of compound (1) is conventional (EP 268,548); compounds (2) through (6) were prepared analogously thereto.

The following examples describe the production of the α-halo-enones of Formula II.

EXAMPLE 1

(1S,2S,3R,5R)-2-[(Z)-(4S)-2-Bromo-4-methyl-3-oxo-1-nonen-6-ynyl]-3-tert-butyldimethylsilyloxy-7,7-(2,2-dimethyltrimethylenedioxy)bicyclo[3.3.0]octane (1)

Preparation

1. Under nitrogen, 4.48 g of sodium hydride (50% in white oil) is introduced into a 1-liter three-necked flask with dropping funnel, "KPG" agitator, and internal thermometer, and a mixture of 93.5 ml of THF and 16.5 ml of toluene is added dropwise.

2. The suspension is cooled to 2° C., and a solution of 22.97 g of (3S)-3-methyl-2-oxo-5-octynylphosphonic acid dimethyl ester in 93.5 ml of THF and 16.5 ml of toluene is added dropwise so that the temperature does not rise above 8° C.

3. 1.3 ml of tetraisopropyl orthotitanate is added to the mixture and the latter is stirred for 45 minutes at 1°-2° C.

4. 20.72 g of N-bromosuccinimide is added all at once, and the mixture is stirred for 45 minutes at 1°-2° C.

5. A solution of 27.5 g of (1S,2S,3R,5R)-7,7-(2,2-dimethyltrimethylenedioxy)-3-tert-butyldimethyl-silyloxybicyclo[3.3.0] octane carbaldehyde in 187 ml of absolute THF and 33 ml of toluene is added dropwise within 15 minutes.

6. The reaction mixture is stirred under ice cooling for 3 hours, then heated over a period of 16 hours to about 15° C.

7. The reaction mixture is adjusted to pH 7 with several drops of glacial acetic acid and concentrated to a volume of about 100 ml on a rotary evaporator.

8. The residue is taken up in 200 ml of water and 200 ml of methyl tert-butyl ether, the aqueous phase is diluted to 800 ml and extracted three times with respectively 150 ml of methyl tert-butyl ether.

9. The methyl tert-butyl ether extracts are washed with 100 ml of water and dried over 80 g of sodium sulfate.

10. The sodium sulfate is filtered off and the mixture rinsed with about 50 ml of methyl tert-butyl ether.

11. The mixture is concentrated, and the residue is chromatographed on 2000 g of silica gel with hexane/ethyl acetate 100:0–80:20.

Yield: 30.73 g = 72.6% of theory

Properties: colorless oil $[\alpha]^{20}$ (c=1, CHCl$_3$) 589 578 546 436 365 nm +19.7° +20.7° +24.2° +48.0° +86.5°

| Analysis: | C | H | Br | % |
|---|---|---|---|---|
| Calcd. | 61.36 | 8.34 | 14.08 | |
| Found | 61.46 | 8.04 | 13.90 | |

The α-halo-enones (2), (3), (4), (5) and (6) were prepared analogously:

EXAMPLE 2

(1S,2S,3R,5R)-2-[(Z)-(4R)-2-Bromo-4-methyl-3-oxo-1-nonen-6-ynyl]-3-tert-butyldimethylsilyloxy-7,7-(2,2-dimethyltrimethylenedioxy)bicyclo[3.3.0]octane (2)

| Analysis: | C | H | Br | % |
|---|---|---|---|---|
| Calcd. | 61.36 | 8.34 | 14.08 | |
| Found | 61.34 | 8.11 | 13.85 | |
| $[\alpha]_D^{20} = -4.4$ (c = 1, CHCl$_3$) | | | | |

EXAMPLE 3

(1S,2S,3R,5R)-2-[(Z)-(4S)-2-Chloro-4-methoxy-3-oxo-1-nonen-6-ynyl]-3-tert-butyldimethylsilyloxy-7,7-(2,2-dimethyltrimethylenedioxy)bicyclo[3.3.0]octane (3)

| Analysis: | C | H | Cl | % |
|---|---|---|---|---|
| Calcd. | 66.57 | 9.05 | 6.78 | |
| Found | 66.76 | 8.95 | 6.78 | |
| $[\alpha]_D^{20} = +11.1$ (c = 1, CHCl$_3$) | | | | |

EXAMPLE 4

(1S,2S,3R,5R)-2-[(Z)-(4R)-2-Chloro-4-methyl-3-oxo-1-nonen-6-ynyl]-3-tert-butyldimethylsilyloxy-7,7-(2,2-dimethyltrimethylenedioxy)bicyclo[3.3.0]octane (4)

| Analysis: | C | H | Cl | % |
|---|---|---|---|---|
| Calcd. | 66.57 | 9.05 | 6.78 | |
| Found | 66.09 | 8.38 | 7.38 | |
| $[\alpha]_D^{20} = -5.0$ (c = 1, CHCl$_3$) | | | | |

EXAMPLE 5

(1S,2S,3R,5R)-2-[(E)-2-Bromo-3-oxo-1-octenyl-3-tert-butyldimethylsilyloxy-7,7-(2,2-dimethyltrimethylenedioxy)bicyclo[3.3.0]octane (5)

| Analysis: | C | H | Br | % |
|---|---|---|---|---|
| Calcd. | 59.65 | 8.71 | 14.70 | |
| Found | 59.94 | 8.40 | 14.34 | |
| $[\alpha]_D^{20} = +4.5$ (c = 1, CHCl$_3$) | | | | |

EXAMPLE 6

(1S,2S,3R,5R)-2-[(Z)-(4S)-2-Bromo-4-methyl-3-oxo-1-nonen-6-ynyl]-3-tert-butyldiphenylsilyloxy-7,7-(2,2-dimethyltrimethylenedioxy)bicyclo[3.3.0]octane (6)

| Analysis: | C | H | Br | % |
|---|---|---|---|---|
| Calcd. | 67.71 | 7.43 | 11.54 | |
| Found | 67.61 | 6.93 | 11.19 | |
| $[\alpha]_D^{20} = +48°$ (c = 1, CHCl$_3$) | | | | |

The conductance of the process according to this invention will be illustrated by the following examples:

EXAMPLE 7

(1S,2S,3R,5R)-2-[(Z)-(3S,4S)-2-Bromo-3-hydroxy-4-methyl-1-nonen-6-ynyl]-3-tert-butyldimethylsilyloxy-7,7-(2,2-dimethyltrimethylenedioxy)bicyclo[3.3.0-octane (7)

Preparation

1. Under nitrogen, 65.46 ml of DIBAL-H T (20% in toluene) is charged into a 500 ml three-necked flask with dropping funnel, "KPG" stirrer, and internal thermometer.

2. The mixture is cooled to 2° C., and a solution of 18.46 g of "Ionol" in 50 ml of toluene is added dropwise in such a way that the temperature does not rise above 4° C.

3. The mixture is stirred for 45 minutes and cooled to −75° C.

4. A solution of 29.73 g of (1S,2S,3R,5R)-2-[(Z)-(4S)-2-bromo-4-methyl-3-oxo-1-nonen-6-ynyl]-3-tert-butyldimethylsilyloxy-7,7-(2,2-dimethyltrimethylenedioxy)-bicyclo[3.3.0]octane in 60 ml of toluene is added within 75 minutes so that the temperature does not rise above −70° C.

5. The orange-colored solution is further stirred at −70° C. for 45 minutes at −75° C.

6. 12 ml of isopropanol is added dropwise, and the cooling bath is removed.

7. At −20° C., 40 ml of saturated sodium bicarbonate solution is gently added dropwise.

8. The mixture is further stirred for 30 minutes, and the thus-formed white suspension is suctioned off in a G4 porous glass plate, dried over sodium sulfate, suctioned off, and concentrated until the weight remains constant.

10. The residue is chromatographed on 2000 g of silica gel with toluene/ethyl acetate 100:0 to 90:10.

Yield: 24.32 g = 81.5% of theory
Properties: colorless oil. [α] (c=1, CHCl₃) 589 578 546 436 365 nm +23.6°+24.3°+28.3°+53.8°+98.1°

| Analysis: | C | H | Br | % |
|---|---|---|---|---|
| Calcd. | 61.14 | 8.67 | 14.02 | |
| Found | 61.36 | 8.28 | 13.40 | |

The following alcohols (8), (9), (10), (11), (12) were produced analogously:

EXAMPLE 8

(1S,2S,3R,5R)-2-[(Z)-(3S,4R)-2-Bromo-3-hydroxy-4-methyl-1-nonen-6-ynyl]-3-tert-butyldimethylsilyloxy-7,7-(2,2-dimethyltrimethylenedioxy)bicyclo[3.3.0]octane (8)

| Analysis: | C | H | Br | % |
|---|---|---|---|---|
| Calcd. | 61.14 | 8.67 | 14.03 | |
| Found | 61.64 | 8.66 | 14.16 | |
| $[\alpha]_D^{20}$ = −15.0 (c = 1, CHCl₃) | | | | |

EXAMPLE 9

(1S,2S,3R,5R)-2-[(Z)-(3S,4S)-2-Chloro-3-hydroxy-4-methyl-1-nonen-6-ynyl]-3-tert-butyldimethylsilyloxy-7,7-(2,2-dimethyltrimethylenedioxy)bicyclo[3.3.0]octane (9)

| Analysis: | C | H | Cl | % |
|---|---|---|---|---|
| Calcd. | 66.32 | 9.40 | 6.75 | |
| Found | 66.64 | 9.25 | 6.60 | |
| $[\alpha]_D^{20}$ = +16.4 (c = 1, CHCl₃) | | | | |

EXAMPLE 10

(1S,2S,3R,5R)-2-[(Z)-(3S,4R)-2-Chloro-3-hydroxy-4-methyl-1-nonen-6-ynyl]-3-tert-butyldimethylsilyloxy-7,7-(2,2-dimethyltrimethyleneidioxy)bicyclo[3.3.0]-octane (10)

| Analysis: | C | H | Cl | % |
|---|---|---|---|---|
| Calcd. | 66.32 | 9.40 | 6.75 | |
| Found | 66.43 | 9.25 | 6.78 | |
| $[\alpha]_D^{20}$ = +30.2 (c = 1, CHCl₃) | | | | |

EXAMPLE 11

(1S,2S,3R,5R)-2-[(Z)-(3S)-2-Bromo-3-hydroxy-1-octenyl]-3-tert-butyldimethylsilyloxy-7,7-(2,2-dimethyltrimethylenedioxy)bicyclo[3.3.0]octane (11)

| Analysis: | C | H | Br | % |
|---|---|---|---|---|
| Calcd. | 59.44 | 9.05 | 14.41 | |
| Found | 59.70 | 8.61 | 14.08 | |
| $[\alpha]_D^{20}$ = +9.4 (c = 1, CHCl₃) | | | | |

EXAMPLE 12

(1S,2S,3R,5R)-2-[(Z)-(3S,4S)-2-Bromo-4-methyl-3-oxo-1-nonen-6-ynyl]-3-tert-butyldiphenylsilyloxy-7,7-(2,2-dimethyltrimethylenedioxy)bicyclo[3.3.0]octane (12)

| Analysis: | C | H | Br | % |
|---|---|---|---|---|
| Calcd. | 67.51 | 7.70 | 11.52 | |
| Found | 67.47 | 7.62 | 11.05 | |
| $[\alpha]_D^{20}$ = +46.0 (c = 1, CHCl₃) | | | | |

The pharmacologically effective cicaprost is prepared according to W. Skuballa et al (J. Med. Chem. 1986, 29:313) from (1S,2S,3R,5R)-3-hydroxy-2-[(3S,4S)-3-hydroxy-4-methyl-1,6-nonadiynyl]bicyclo-[3.3.0]octan-7-one which latter is obtained from the compounds of Formula I by base-catalyzed HX elimination and subsequent acid-catalyzed cleavage of the blocking groups (ketal, silyl ether). The two last process steps are known from the literature.

We claim:

1. A process for the preparation of (1S,2S,3R,5R)-2-[(3S)-2-halo-3-hydroxy-1-alken(ynyl)]-3-trialkyl-silyloxy-7,7-(2,2-dimethyltrimethylenedioxy)-bicyclo[3.3.0]octane compounds of Formula I

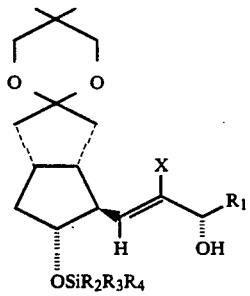

wherein
X is chlorine or bromine,
R₁ is a straight-chain or branched alkyl of up to 7 carbon atoms, straight-chain or branched alkenyl of up to 7 atoms, straight-chain or branched alkynyl of up to 7 atoms,
R₂, R₃, R₄ is in each case identical or different and is C₁–C₄-alkyl and phenyl optionally substituted by C₁–C₄-alkyl groups, wherein the 13,14-double bond has the trans configuration with respect to the C chain, by stereoselective reduction of an α-halo-enone of general Formula II

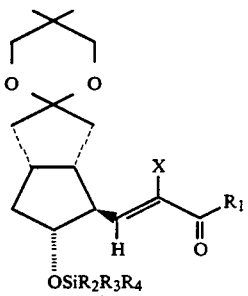

wherein X, R₁, R₂, R₃, R₄ have the meanings given above, with diisobutylaluminum 2,6-di-tert-butyl-4-methylphenoxide, wherein the reaction is conducted at −40° C. to −100° C.

2. A process comprising reacting by stereoselective reduction an α-halo-enone of Formula II

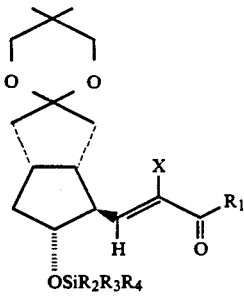

wherein
X is chlorine or bromine,
R₁ is a straight-chain or branched alkyl of up to 7 carbon atoms, straight-chain or branched alkenyl of up to 7 atoms, straight-chain or branched alkynyl of up to 7 atoms,
R₂, R₃, R₄ is in each case identical or different and is C₁–C₄-alkyl and phenyl optionally substituted by C₁–C₄-alkyl groups, wherein the 13,14-double bond has the trans configuration with respect to the C chain,
with diisobutylaluminum 2,6-di-tert-butyl-4-methylphenoxide, wherein the reaction is conducted at −40° C. to −100° C., forming (1S,2S,3R,5R)-2-[(3S)-2-halo-3-hydroxy-1-alken(ynyl)]-3-trialkylsilyloxy-7,7-(2,2-dimethyltri-methylenedioxy)bicyclo[3.3.0]octane compounds of general Formula I

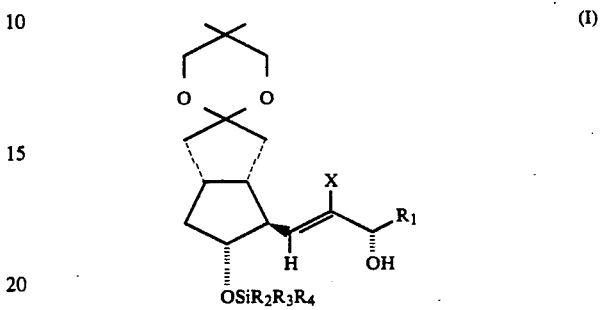

wherein X, R₁, R₂, R₃, R₄ have the meanings given above.

3. A process according to claim 1, wherein the reaction is conducted in toluene.

4. A process according to claim 1, wherein 1.1–1.5 equivalents of diisobutylaluminum 2,6-di-tert-butyl-4-methylphenoxide are employed.

5. A process according to claim 1, wherein R₂ is tert butyl and R₃ and R₄ each are methyl or phenyl.

6. A process of claim 1, wherein R₁ is hexyl-2-ynyl.

7. A process of claim 6, wherein R₂ is tert butyl and R₃ and R₄ each are methyl or phenyl; wherein 1.1–1.5 equivalents of diisobutylaluminum 2,6-di-tert-butyl-4-methylphenoxide are employed; and wherein the reaction is conducted at −70° C. to −80° C.

8. The process of claim 1 for preparing the compounds of Formula I, wherein
R₁ is

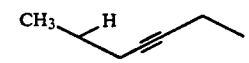

R₂ is t-butyl;
R₃ is methyl;
R₄ is methyl;
X is Br or Cl.

9. The process of claim 1 for preparing the compound of Formula I wherein
R₁ is

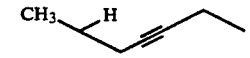

R₂ is t-butyl;
R₃ is phenyl;
R₄ is phenyl;
X is Br.

10. The process of claim 1 where R₁ contains up to 6 carbon atoms.

11. The process of claim 1 further comprising conventionally converting an obtained compound of Formula I to cicoprost or eptaloprost.

12. The process of claim 2 further comprising conventionally converting the compound of formula I to cicoprost or eptaloprost.

* * * * *